(12) United States Patent
Liu

(10) Patent No.: US 6,976,275 B1
(45) Date of Patent: Dec. 20, 2005

(54) PROTECTIVE EAR SHIELD

(76) Inventor: Chin Chia Liu, 275 6th St. Apt. #120, Tustin, CA (US) 92780

( * ) Notice: Subject to any disclaimer, the term of this patent is extended or adjusted under 35 U.S.C. 154(b) by 12 days.

(21) Appl. No.: 10/857,680

(22) Filed: May 29, 2004

(51) Int. Cl.[7] .............................................. A42B 1/08
(52) U.S. Cl. ............................................ 2/423; 2/209
(58) Field of Search ........................... 2/423, 209, 174, 2/208, 455, DIG. 11; 128/864, 866; 132/319, 132/212, 213, 333, 270

(56) References Cited

U.S. PATENT DOCUMENTS

| 2,729,823 | A | * | 1/1956 | Foster | 2/174 |
|---|---|---|---|---|---|
| 4,751,746 | A | | 6/1988 | Rustin | |
| 5,119,514 | A | | 6/1992 | Woehl | |
| 5,619,750 | A | | 4/1997 | Allewalt | |
| 5,673,438 | A | | 10/1997 | Lambert | |
| 5,943,703 | A | | 8/1999 | Avila, Jr. | |
| 6,195,806 | B1 | * | 3/2001 | Campbell | 2/209 |
| 6,325,173 | B1 | | 12/2001 | Miller | |
| 6,418,565 | B1 | * | 7/2002 | Tsujino | 2/425 |
| 6,505,633 | B2 | * | 1/2003 | Mosely | 132/319 |
| 6,510,230 | B2 | * | 1/2003 | Marx | 381/189 |
| 6,550,064 | B2 | | 4/2003 | Schmitt et al. | |

* cited by examiner

Primary Examiner—Tejash Patel

(57) ABSTRACT

A protective ear shield releasably mounted over the top and the rear saddleback portion of an ear suitable for releasing discomfort due to compression pressure of the shield and the weight of the added body accessory. The protective ear shield comprises at least two curved sections joined with an adjustable connecting member for adjusting and fixing the distance between these two sections. The ear shield is configured to fit the contours of the top and the rear saddleback portion of the ear so as to minimize the discomfort feeling. The ear shield may comprise a hook element at each end of the two sections configured for securing the eyeglasses or sunglasses.

20 Claims, 6 Drawing Sheets

PROTECTIVE EAR SHIELD

FIELD OF THE INVENTION

The present invention generally relates to a protective ear shield apparatus. More particularly, the present invention relates to the ear shield and methods of use with at least one hook element that is secured at a rear saddleback portion of the shield suitably configured for eliminating or evenly distributing the compressive pressure resulted from the weight of the shield, the hook elements, or the body accessories attached on the hook element.

BACKGROUND OF THE INVENTION

In everyday life, it is common to use the ear to support or hang some apparatus around the face, such as a pair of supportive bars on eyeglasses, or supportive elastic loops of a mouth mask. In the process of using the apparatus, some undue pressure is exerted onto a narrow portion of the ear causing concentrated focal pressure and discomfort. The main cause of discomfort comes from compressive pressure from a limited contact surface of the apparatus onto the ear. Over a long duration, the concentrated pressure is troublesome and unbearable to the wearers.

U.S. Pat. No. 5,619,750, entire contents of which are incorporated herein by reference, discloses a safety equipment allowing simultaneous protection of a wearer's eyes, ears and nose from environmental influence, particularly, from sunlight.

U.S. Pat. No. 6,550,064, entire contents of which are incorporated herein by reference, discloses an ear shield assembly which attaches to various headgear and protects the users' ears against the sun and ultra violet rays, thereby reducing the probability of inducing cancer in this normally sensitive and exposed area. The ear shields are placed above the ears and extended outward horizontally from the brim of the cap, allowing air to reach the users' ears, while at the same time blocking the sunlight from reaching the ears.

U.S. Pat. No. 5,673,438, entire contents of which are incorporated herein by reference, discloses an ear shield assembly comprising a headband fabricated of semi-rigid material and formed in a generally semi-circular configuration; and two ear covers each formed in a hollow generally semi-spherical configuration, each ear covering having a concave inner surface and a convex outer surface, a free end of the headband being coupled through each ear cover, in an operative orientation a user placing the headband across his forehead, the user then positioning each ear cover over the auricle of an ear, the apparatus protecting a user's forehead and ears from hair dye during hair coloring.

U.S. Pat. No. 6,325,173, entire contents of which are incorporated herein by reference, discloses a method of alleviating the sound masking effects of wind noise on a cyclist wearing a safety helmet. The ear cover shield has a generally smooth exterior side that is positioned adjacent to but generally spaced from an ear of the cyclist so that wind is generally deflected from the ear so that the noise of air rushing over the ear is substantially reduced, and the cyclist is better able to hear the sound generated from directions which he cannot readily see.

U.S. Pat. No. 5,943,703, entire contents of which are incorporated herein by reference, discloses an ear protector with a flexible element preferably made of PVC, having a first enlarged section used for covering over an ear, and a second, forwardly-extending, reduced mounting section extending from the first enlarged section. Each section has formed therein a vertical slit, forming together a pair of forwardly-positioned slits through which may be passed the temple part of eyeglasses or sunglasses.

U.S. Pat. No. 4,751,746, entire contents of which are incorporated herein by reference, describes a protector, preferably for skiers, which can be readily mounted on a temple of glasses and extends from the front of the glasses to and beyond the ear piece of the temple so that there will be protection against wind and sun for a wearer's eyes, the side of the face and ears. The protector is formed of a cloth having insulating characteristics.

The prior art teaches an ear protector preventing a wearer's ears from being injured by an excessive sunlight, wind, or the like. None of them discloses an ear shield apparatus that could be suitably configured for eliminating or evenly distributing the compressive pressure resulted from the weight of the shield and the body accessory, such as a pair of eyeglasses.

SUMMARY OF THE INVENTION

It is one object of the present invention to provide an ear shield suitable for eliminating or evenly distributing the compressive pressure from the shield onto the ear, comprising an outer contour surface configured and curved to substantially follow a shape of the rear saddleback portion of a human ear.

In a further embodiment, the ear shield comprises an upper end section and a lower end section joined with an adjustable connecting member for adjusting and fixing the distance between these two sections. In one embodiment, the adjustable connecting member comprises a set of bolt and nuts for fixing the distance between the two shield elements.

In a further embodiment, the ear shield comprises at least one first hook element secured to about the upper end section of the outer curved surface and a second hook element secured to about the lower end section of the outer curved surface.

In a further embodiment, the ear shield comprises at least one hanger or grasper for firmly holding any body accessory at about the upper end section with a hanger/grasper stopper.

Some aspects of the invention relate to an ear shield apparatus comprising a pair of ear shields that is connected by a flexible string, thread, or connector.

BRIEF DESCRIPTION OF THE DRAWINGS

Further features and advantages of the present invention will become apparent to one of skill in the art in view of the Detailed Description of Exemplary Embodiments that follows, when considered together with the attached drawings and claims.

DETAILED DESCRIPTION OF EXEMPLARY EMBODIMENTS

The preferred embodiments of the present invention described below relate particularly to an ear shield apparatus that is curved to substantially follow a shape of a rear saddleback portion of the human ear suitably configured for eliminating or evenly distributing the compressive pressure resulted from the weight of the shield and/or the body accessory. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

Figure 1:
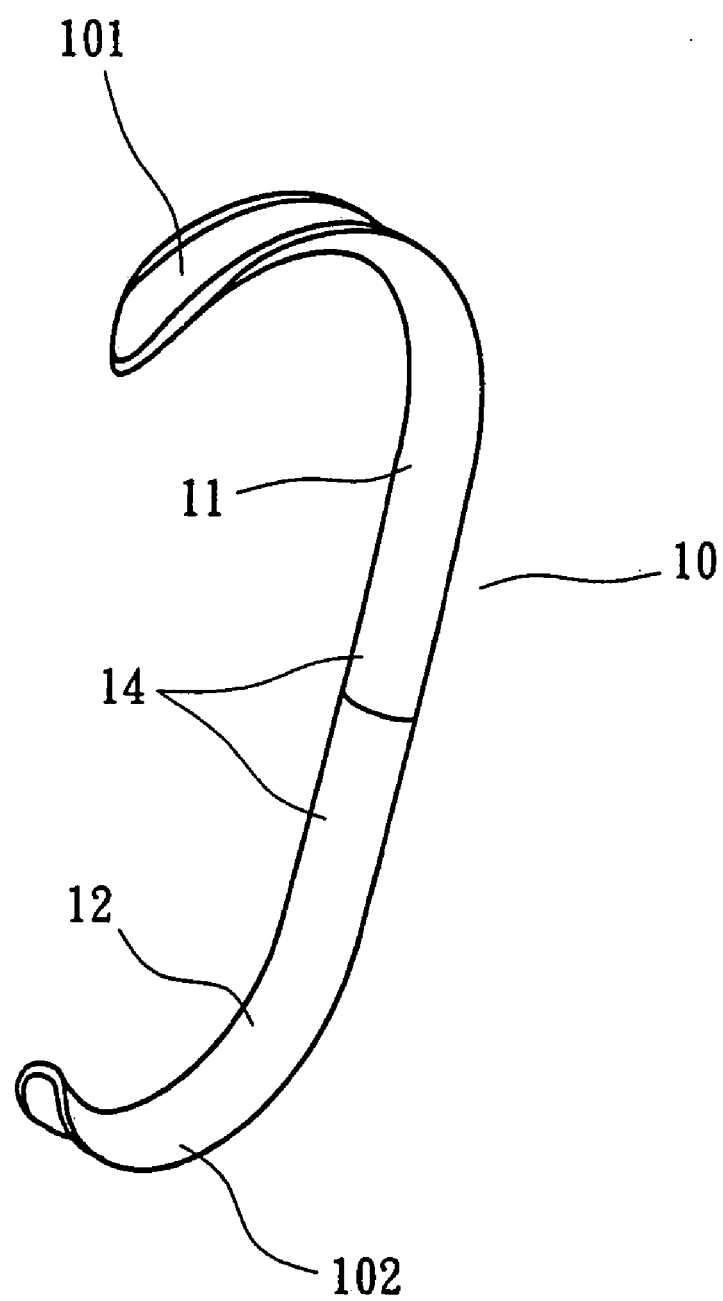
FIG. 1 is a perspective view of the ear shield according to the principles of the present invention.
Figure 2:
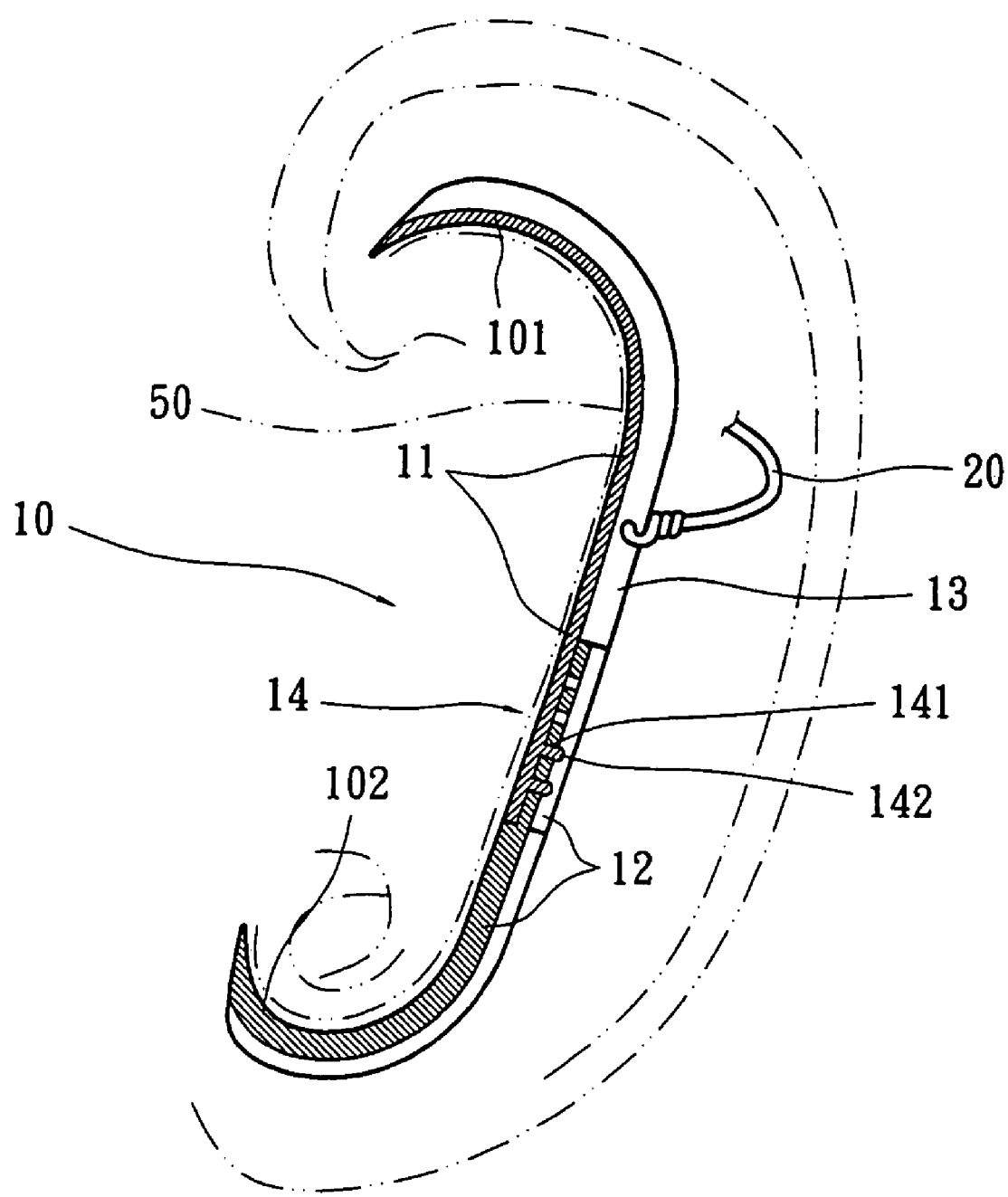
FIG. 2 is a partial cross-sectional view of the ear shield with an adjustable connecting member for adjusting and fixing a first distance between the upper and lower shield elements.
Figure 3:
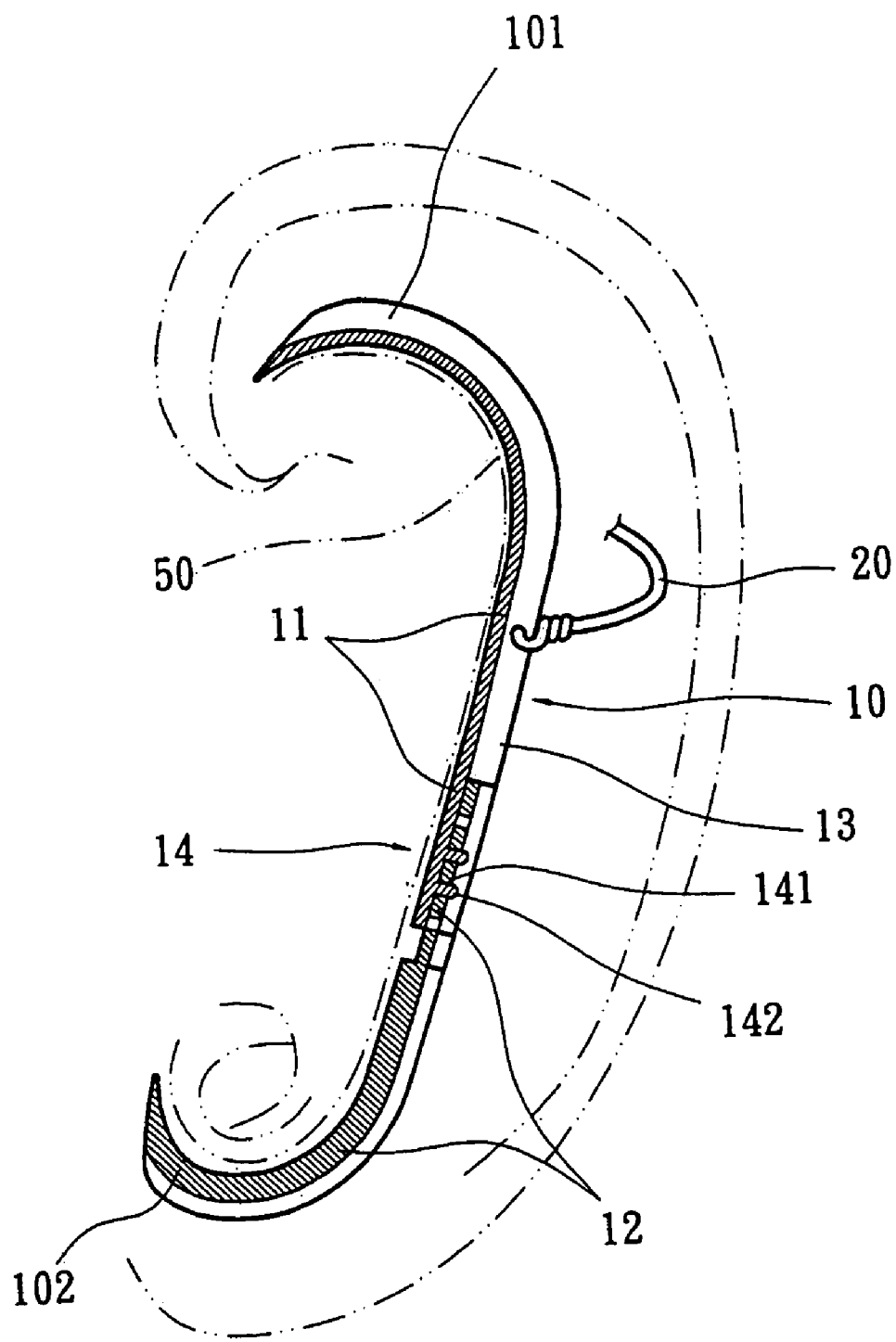
FIG. 3 is a partial cross-sectional view of the ear shield with an adjustable connecting member for adjusting and fixing a second distance between the upper and lower shield elements.

Referring to FIGS. 1–3, what is shown is an embodiment comprising an ear shield (10) that is curved and configured to substantially follow a shape of the ear from the top of the ear and down to the rear saddleback portion of the ear (that is, over the auricle of a human ear). In one preferred embodiment, the contour shape of the rear saddleback portion (50) of the shield snuggly matches the rear saddleback portion of the human ear. The shield (10) comprises an upper end section (101) and a lower end section (102), wherein at least one hook element is mounted or secured at about the upper end section and the lower end section of the shield. Preferably, the cross-section of either end section is narrower than the cross-section of the middle section (13). The shield further comprises an outer curved surface that faces away from the ear, wherein the outer surface has an upper end section and a lower end section, the ear shield having an inner contour surface facing a human ear, wherein the inner surface is configured to substantially follow a shape of a rear saddleback portion of a human ear.

In one embodiment, the inner counter surface is bowed inwardly in a concave manner for positioning the ear shield against the ear, whereby the ear shield is snuggly positioned against the ear following the shape of the rear saddleback portion of an ear.

In another embodiment, the ear shield (10) comprises an upper shield element (11) having an upper end section (101) and a lower shield element (12) having a lower end section (102), wherein the upper and lower shield elements are joined with an adjustable connecting member (14) for adjusting and fixing the distance between these two sections. In one embodiment, the adjustable connecting member comprises a set of bolt (142) and nuts (141). The distance between the two shield elements is determined by inserting the bolt into one of the nuts. FIG. 2 shows a partial cross-sectional view of the ear shield with an adjustable connecting member (14) for adjusting and fixing a first distance between the upper and lower shield elements, while FIG. 3 shows a second distance between the upper and lower shield elements that is longer than the first distance.

Figure 4:
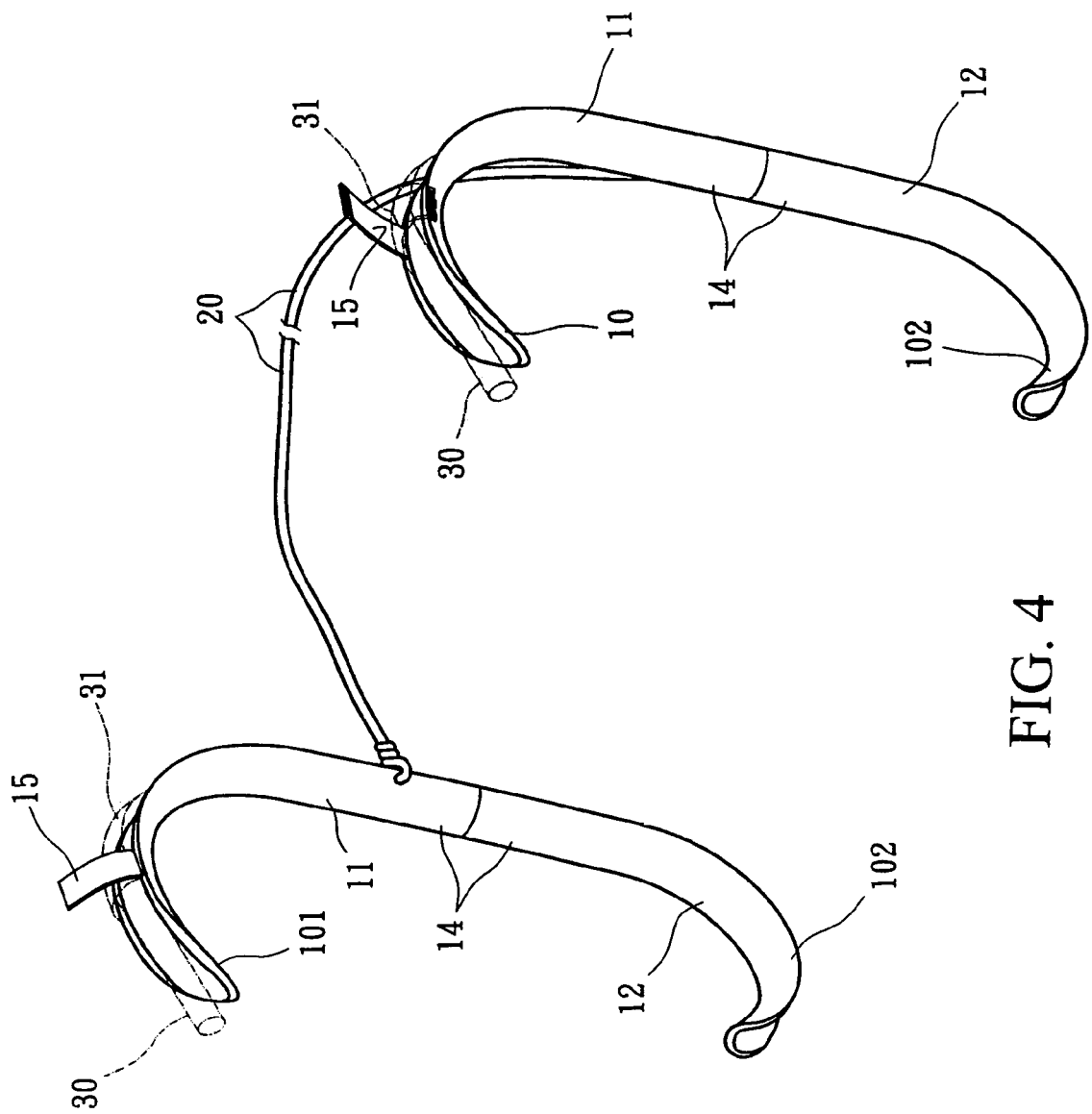
FIG. 4 is a perspective view of the ear shield apparatus comprising two ear shields connected with a flexible string.
Figure 5:
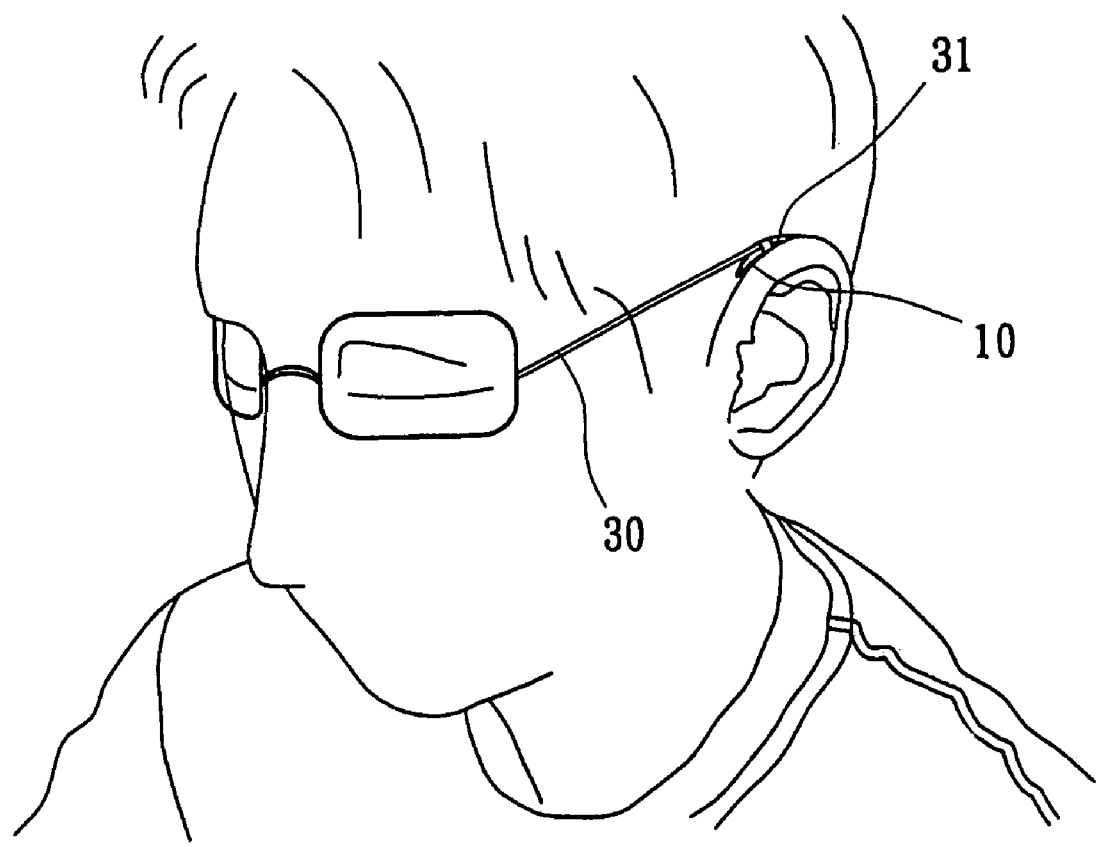
FIG. 5 is a perspective view of the ear shield apparatus worn by an individual comprising two ear shields connected to a pair of eyeglasses.
Figure 6:
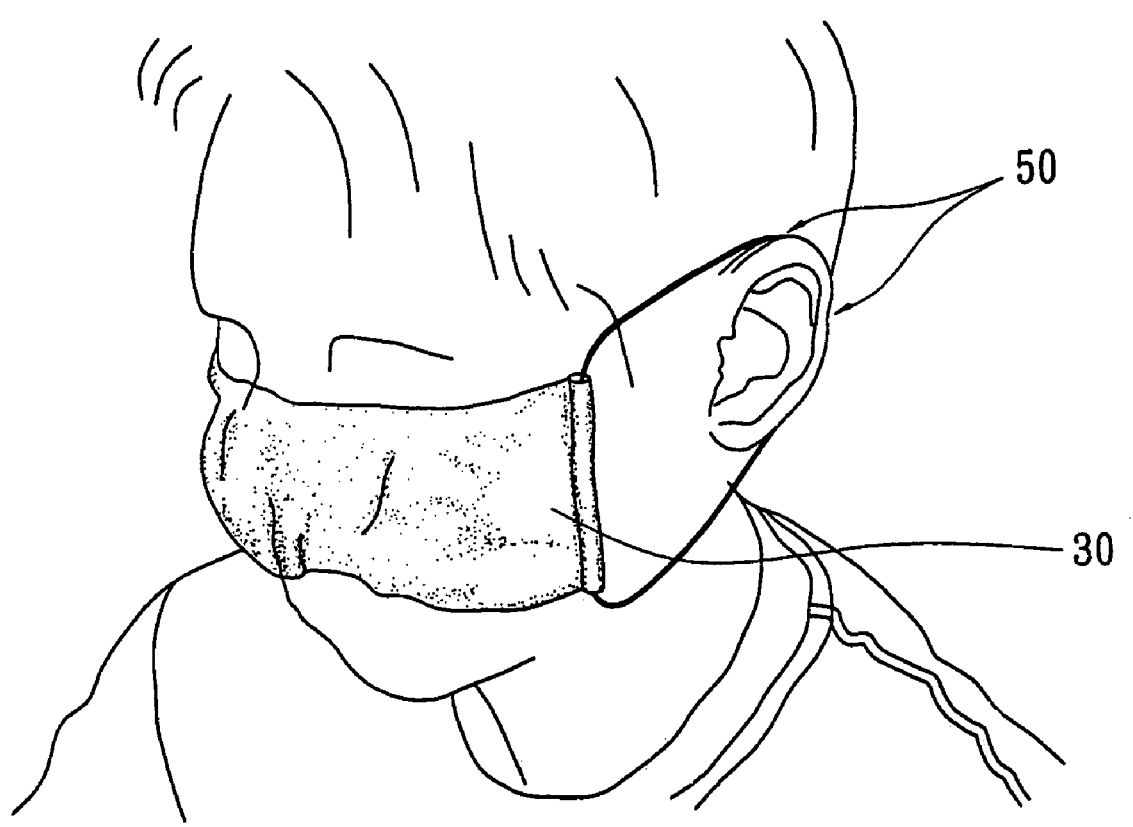
FIG. 6 is a perspective view of the ear shield apparatus worn by an individual comprising two ear shields connected to a mouth mask.

Furthermore, the ear shield apparatus comprises a pair of identical ear shields, wherein the first shield is connected to the second shield with a flexible string or thread (20). FIG. 4 shows a perspective view of the ear shield apparatus comprising two ear shields connected with a flexible string. Each shield (10) is equipped with at least one hanger or grasper (31) at about the upper end section (101) for holding or securing a body accessory (30), such as a pair of eyeglasses as a sight-aid or a mouth mask as a breath-protecting-aid, wherein there is a hanger stopper or grasper stopper (15) located adjacent to the hanger for releasably holding the body accessory. When the body accessory is released from the ear shield apparatus, the flexible string (20) keeps the body accessory over the neck of the wearer so as to prevent the body accessory from dropping on the floor.

Some aspects of the invention relate to a method for wearing a body accessory (for example, a pair of eyeglasses, a mouth mask, and the like) over the ear with desired evenly distributed compressive pressure comprising: (a) providing an ear shield apparatus comprising a first ear shield and a second ear shield (10), each ear shield having an outer curved surface, an inner contour surface facing a human ear, and at least one hanger/grasper secured to about the upper end section of each shield; (b) placing the ear shield over the rear saddleback portion of the ear; (c) connecting the flexible string to both ear shields; and (d) securing the body accessory (30) on the hanger (31) of the shield (10). Therefore, the body accessory (30) on the hanger (31) is kept away by the ear shield and would not contact and press onto the rear saddleback portion of the ear. In other words, the weight of the body accessory is distributed evenly over the more surface area of the rear saddleback portion of the ear rather than on the conventional narrow concave zone between the ear and the head.

Furthermore, the flexible string (20) and the hanger stopper (15) is appropriately located on the upper shield element of the ear shield and configured to provide easy and convenient operations for releasing the body accessory from the ear shield apparatus while holding the body accessory over the neck of the wearer.

From the foregoing description, it will be appreciated that an ear shield apparatus of a generally curved shape and methods of use has been disclosed. While aspects of the invention have been described with reference to specific embodiments, the description is illustrative and is not intended to limit the scope of the invention. Various modifications and applications of the invention may occur to those who are skilled in the art, without departing from the true spirit or scope of the invention. The breadth and scope of the invention should be defined only in accordance with the appended claims and their equivalents.

What is claimed is:

1. An ear shield apparatus of a generally curved shape comprising: a first ear shield having an outer curved surface, wherein said outer surface has an upper end section and a lower end section; said first ear shield having an inner contour surface facing a human ear, wherein the inner surface is configured to substantially follow a shape of a rear saddleback portion of a human ear; and at least one first hook element secured to about the upper end section of said outer curved surface, wherein the first shield comprises an upper shield element and a lower shield element, the two shield elements being joined together with an adjustable connecting member for adjusting and fixing the distance between the two shield elements.

2. The ear shield apparatus according to claim 1, further comprising a second shield identical to the first shield, wherein the first shield is connected to the second shield with a flexible string.

3. The ear shield apparatus according to claim 2, wherein the first shield or the second shield further comprises at least one hanger at about the upper end section with a hanger stopper.

4. The ear shield apparatus according to claim 1, further comprising a second shield identical to the first shield, wherein the first shield is connected to the second shield with a flexible string.

5. The ear shield apparatus according to claim 4, wherein the first shield or the second shield further comprises at least one hanger at about the upper end section with a hanger stopper.

6. The ear shield apparatus according to claim 1, wherein the adjustable connecting member comprises a set of bolt and nuts for fixing the distance between the two shield elements.

7. The ear shield apparatus according to claim 2, wherein each of the first shield and the second shield comprises an upper shield element and a lower shield element, the two shield elements being joined together with an adjustable connecting member for adjusting and fixing the distance between the two shield elements, and wherein the adjustable connecting member comprises a set of bolt and buts for fixing the distance between the two shield elements.

8. The ear shield apparatus according to claim 3, wherein each of the first shield and the second shield comprises an upper shield element and a lower shield element, the two shield elements being joined together with an adjustable connecting member for adjusting and fixing the distance between the two shield elements, and wherein the adjustable connecting member comprises a set of bolt and nuts for fixing the distance between the two shield elements.

9. The ear shield apparatus according to claim 4, wherein each of the adjustable connecting members in the first shield and the second shield comprises a set of bolt and nuts for fixing the distance between the two shield elements.

10. The ear shield apparatus according to claim 5, wherein each of the adjustable connecting members in the first shield and the second shield comprises a set of bolt and nuts for fixing the distance between the two shield elements.

11. An ear shield apparatus of a generally curved shape comprising: a first ear shield having an outer curved surface, wherein said outer surface has an upper end section and a lower end section; said first ear shield having an inner contour surface facing a human ear, wherein the inner surface is configured to substantially follow a shape of a rear saddleback portion of a human ear; and at least one first hook element secured to about the upper end section of said outer curved surface, further comprising a second hook element secured to about the lower end section of said outer curved surface, wherein the first shield comprises an upper shield element and a lower shield element, the two shield elements being joined together with an adjustable connecting member for adjusting and fixing the distance between the two shield elements.

12. The ear shield apparatus according to claim 11, further comprising a second shield identical to the first shield, wherein the first shield is connected to the second shield with a flexible string.

13. The ear shield apparatus according to claim 12, wherein the first shield or the second shield further comprises at least one hanger at about the upper end section with a hanger stopper.

14. The ear shield apparatus according to claim 11, further comprising a second shield identical to the first shield, wherein the first shield is connected to the second shield with a flexible string.

15. The ear shield apparatus according to claim 14, wherein the first shield or the second shield further comprises at least one hanger at about the upper end section with a hanger stopper.

16. The ear shield apparatus according to claim 11, wherein the adjustable connecting member comprises a set of bolt and nuts for fixing the distance between the two shield elements.

17. The ear shield apparatus according to claim 12, wherein each of the first shield and the second shield comprises an upper shield element and a lower shield element, the two shield elements being joined together with an adjustable connecting member for adjusting and fixing the distance between the two shield elements, and wherein the adjustable connecting member comprises a set of bolt and buts for fixing the distance between the two shield elements.

18. The ear shield apparatus according to claim 13, wherein each of the first shield and the second shield comprises an upper shield element and a lower shield element, the two shield elements being joined together with an adjustable connecting member for adjusting and fixing the distance between the two shield elements, and wherein the adjustable connecting member comprises a set of bolt and nuts for fixing the distance between the two shield elements.

19. The ear shield apparatus according to claim 14, wherein each of the adjustable connecting members in the first shield and the second shield comprises a set of bolt and nuts for fixing the distance between the two shield elements.

20. The ear shield apparatus according to claim 15, wherein each of the adjustable connecting members in the first shield and the second shield comprises a set of bolt and nuts for fixing the distance between the two shield elements.

\* \* \* \* \*